United States Patent [19]

Conway et al.

[11] 4,312,360
[45] Jan. 26, 1982

[54] DEVICE TO AID IN THE DETERMINATION OF OVULATION IN A FEMALE MAMALIAN

[76] Inventors: Julian C. Conway, 1369 Vue De Ville Ct.; James Andrews, 1344 Vue De Ville Ct., both of San Diego, Calif. 92109

[21] Appl. No.: 124,590

[22] Filed: Feb. 25, 1980

[51] Int. Cl.³ ............................................. A61B 5/04
[52] U.S. Cl. ................................. 128/736; 128/738
[58] Field of Search ............. 128/736, 738; 73/362 R, 73/362 AR, 362 SC; 324/71 R, 72

[56] References Cited

U.S. PATENT DOCUMENTS

| | | | |
|---|---|---|---|
| 4,050,308 | 9/1977 | Lee | 73/362 A |
| 4,109,643 | 8/1978 | Bond et al. | 128/666 |
| 4,148,304 | 4/1979 | Mull | 128/738 |
| 4,151,831 | 5/1979 | Lester | 128/738 |
| 4,203,452 | 5/1980 | Cohen | 128/732 |

*Primary Examiner*—Robert W. Michell
*Assistant Examiner*—Francis J. Jaworski
*Attorney, Agent, or Firm*—Brown & Martin

[57] ABSTRACT

A body voltage measurement circuit and body temperature measurement circuit are simplified to the point that they can be both included in a single low cost hand held package through the use of twin voltage ladder output circuits. The temperature and voltage measurements circuits are functionally joined together by virtue of the fact that the temperature probe of the temperature measurement circuit is used as a common mode rejection voltage reference for the differential amplifier in the voltage measurement circuit.

10 Claims, 3 Drawing Figures

DEVICE TO AID IN THE DETERMINATION OF OVULATION IN A FEMALE MAMALIAN

BACKGROUND OF THE INVENTION

This invention relates to body voltage and body temperature measurement instruments.

It has been found in laboratory tests that ovulation in mammals, including humans, is accompanied by a small but measurable rise in body temperature and a small but measurable rise in the voltage between spaced apart points on the exterior of the body, e.g. between the thumbs. In recent years, efforts have been made to utilize these two effects to detect ovulation in humans for use in the rhythm method of birth control. The rhythm method of birth control requires that couples abstain from intercourse for a period before and after ovulation. It is believed that the ovum is susceptible to fertilization for about 24 hours after its release, and that the sperm deposited in the female reproductive tract is capable of fertilizing the ovum for about 72 hours. Thus if intercourse does not occur from three days before ovulation to one day after ovulation, the sperm cannot fertilize the ovum and conception will not take place.

The difficulty in practicing the rhythm method is that ovulation time differs in every woman, and although there are laboratory instruments for detecting the onset of ovulation, there are no presently available consumer instruments that can be used by the average woman. Various consumer instruments have been proposed, some utilizing temperature alone, some utilizing voltage alone, and some utilizing both. The instruments which work by voltage or temperature alone are unreliable because there are reasons why a woman's temperature, or voltage, will rise other than ovulation. The instruments which take both temperature and voltage into consideration will, it is believed, probably correctly identify ovulation by the correlation between a temperature rise and a voltage rise, which will eliminate those physiological events which cause a rise of temperature alone, or of voltage alone. The difficulty with the type of instrument which utilizes both indications is that the presently proposed consumer designs are relatively complex and costly and thus would be available only to the wealthy. The principal object of this invention is to provide an instrument for detecting ovulation in terms of both body temperature and voltage which is low enough in cost to be available to the average woman.

Another object of this invention is to provide an instrument of the above noted type which is small enough to be held in the hand.

A further object of this invention is to provide an instrument of the above noted type which is simple to read and to operate.

Other objects and advantages of the invention will be apparent from the detailed description of the invention herein.

SUMMARY OF THE INVENTION

In accordance with this invention, a small, low-cost instrument is provided by using a voltage ladder output circuit in both the voltage measurement circuit and the temperature measurement circuit. A plurality of output indicators is provided for each voltage ladder output circuit. Each output indicator is coupled to a separate rung of the voltage ladder circuit and the total number of indicators which are lit represents the magnitude of voltage and temperature. This is a simple output circuit which enables both the voltage measurement circuit and the temperature measurement circuit to be packaged together in a small hand held package and is easy for the user to interpret. This output circuit uses inexpensive standard components.

DESCRIPTION OF THE PREFERRED EMBODIMENT

Figure 1:
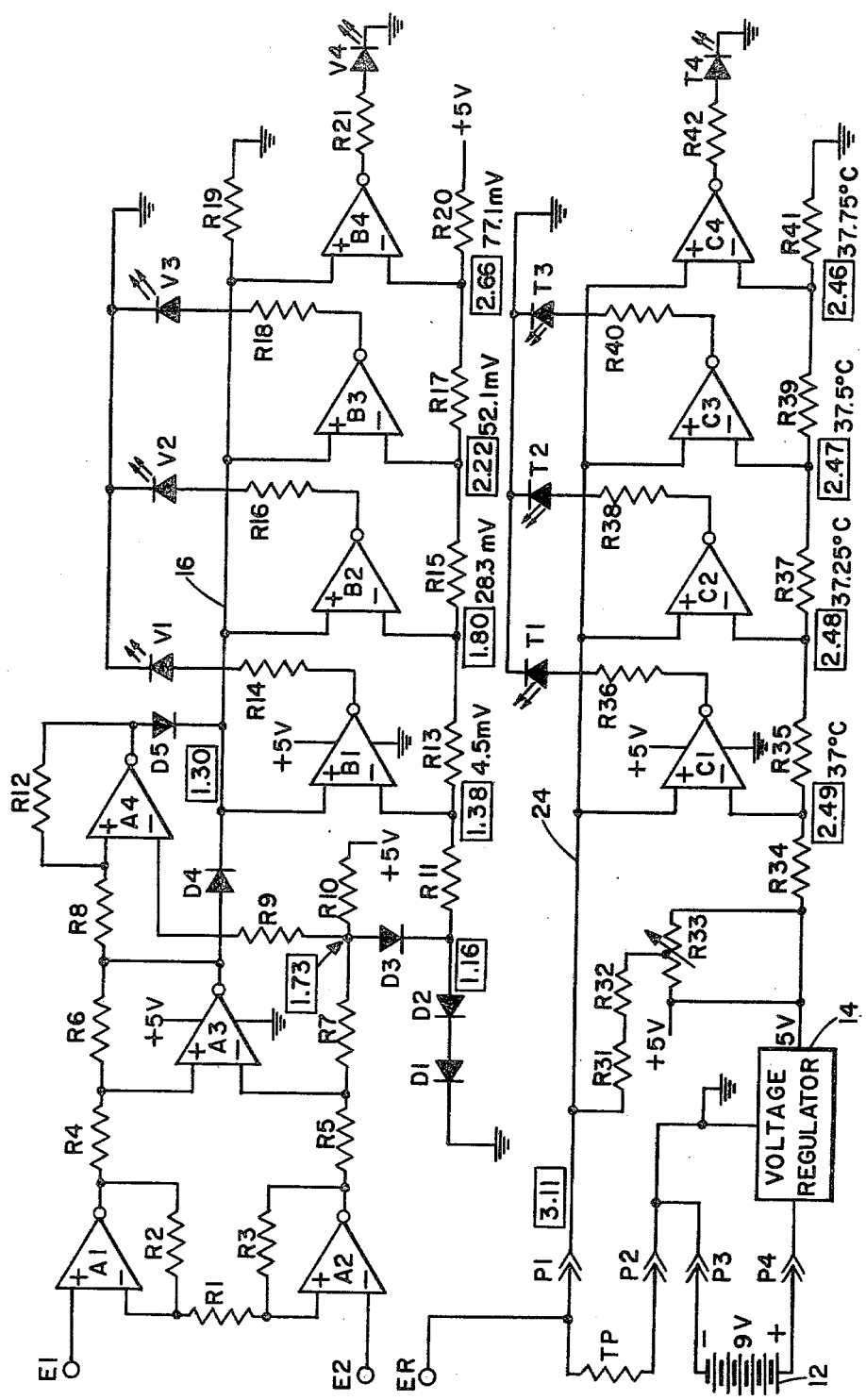
FIG. 1 is a schematic circuit diagram of the preferred embodiment of the invention.
Figure 2:
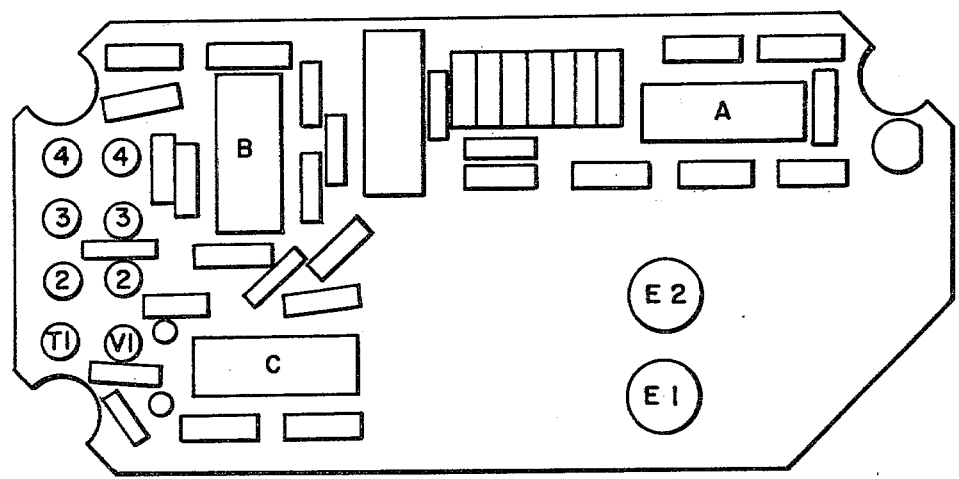
FIG. 2 is a plan view of a printed circuit board upon which the circuit of FIG. 1 is mounted.
Figure 3:
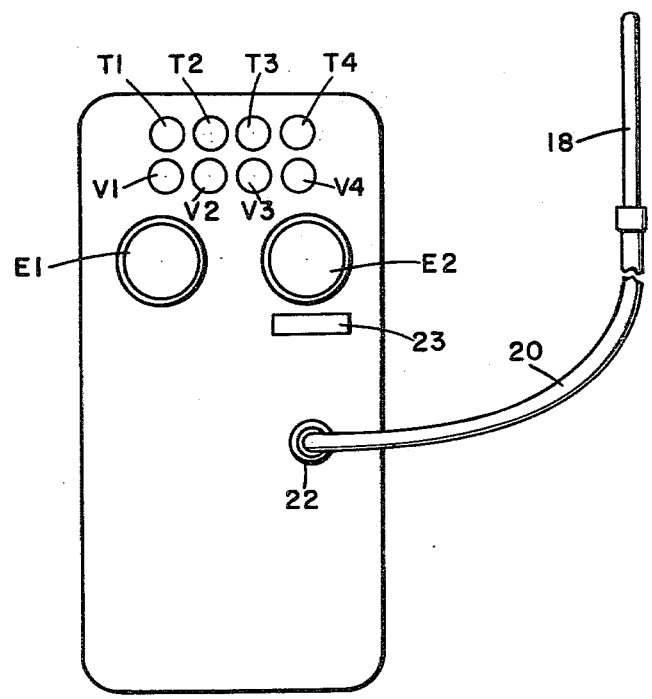
FIG 3 is a plan view of a housing for the circuit of FIGS. 1 and 2.

Referring to FIG. 1, the voltage measurement circuit is shown in the upper part of the drawing and the temperature measurement circuit is shown in the lower part of the drawing. The voltage measurement circuit includes a standard differential amplifier formed by the comparators A1, A2, A3, and resistors R1, R2, R3, R4, R5, R6, and R7. The input to the differential amplifier is applied to terminals E1 and E2, which are mounted on the exterior of the housing 10 as shown in FIG. 3. The user places her thumbs on terminals E1 and E2 while holding housing 10 in both hands to provide an input for the differential amplifier. The output voltage of the differential amplifier is taken at the output of comparator A3 and is given by the equation:

$$E_o = (1 + \frac{2R2}{R1})(E_1 - E_2)$$

Where E1 is the voltage on terminal E1, and E2 is the voltage on terminal E2. The common mode rejection of this particular differential amplifier design is quite high.

The power for the differential amplifier circuit is provided by a battery 12 (in the lower part of FIG. 1), a 5 volt voltage regulator 14 which is coupled to battery 12, and a voltage divider network comprising resistor R10 and diodes D1, D2, and D3 (in the upper part of FIG. 1).

The output of the differential amplifier appears at the output of comparator A3 and is applied in parallel to an inverter and an output circuit. The inverter is formed by comparator A4 and resistors R8, R9, and R12, which form a unity gain inverting amplifier. The purpose of the inverter is to make the circuit insensitive to the polarity of the voltage difference which appears between terminal E1 and E2. The polarity of the voltage field between terminals E1 and E2 will change from time to time and it is desired to measure only the magnitude of the voltage regardless of its polarity.

The most important feature of this circuit is the output circuit. The output of the differential amplifier and the inverter are coupled in parallel to the output circuit through diodes D4 and D5. The output circuit includes comparators B1, B2, B3, and B4, resistors R11, R13, R14, R15, R16, R17, R18, R19, R20 and R21, and light emitting diodes V1, V2, V3, and V4. The output circuit includes a voltage divider ladder formed by resistors R11, R13, R15, R17, and R20 which are connected between plus 5 volts (on the right in FIG. 1) and 1.16 millivolts at the anode of D2 (on the left in FIG. 1). R11 is 470 ohms, R13, R15, and R17 are 1.0 Kohms each, and R20 is 5.0 Kohms. The voltage at each rung of the ladder is noted in FIG. 1 by the boxed numbers, which specify millivolts. The numbers specifying millivolts to the right of each boxed number specifies the calculated voltage difference between input terminals E1 and E2 for each rung of the ladder.

At each rung of the voltage divider ladder, the negative input terminal of a corresponding comparator B1 through B4 is coupled. All of the positive input terminals of the comparator are coupled in parallel to an output bus 16 which is coupled to the cathodes of diodes D4 and D5 and thus receives the output voltage of the differential amplifier. The output of each comparator is applied to a corresponding one of the light emitting diodes V1 through V4 through a current limiting resistors R14, R16, R18, and R21. R19 is a pull down resistor.

When the instrument is used, the user holds housing 10 in both hands and places her opposite thumbs on the input terminal E1 and E2 to apply input to the differential amplifier. The common mode signals that appear on both terminals E1 and E2 are rejected by the differential amplifier. The voltage differential between the signals on terminals E1 and E2 is amplified by an amplification factor of 17.67 and the output appears at the output of comparator A3 which is applied through diode D4 directly to output bus 16, or, if the polarity of the voltage changes, through the inverting amplifier and diodes D5 to output bus 16. At output bus 16, the voltage is compared to the voltage at each rung of the voltage divider ladder formed by resistors R11, R13, R15, R17, and R20. As the voltage rises to a level equal to the rung of a ladder, it will cause the corresponding light emitting diode to light. As the voltage rises higher, the next light emitting diode to the right of FIG. 1 will light and so on until all four are lit. The level of the voltage in this output circuit is determined not in terms of numbers of millivolts but in terms of numbers of lights. The user is, after all, not concerned with the number of millivolts, but rather with the relative voltage and is concerned with the problem detecting the rise in relative voltage which signifies the onset of ovulation. This rise in voltage can be observed as well by observing the number of lights lit as in knowing the exact number of millivolts which cause the change in the output light.

In this particular design of the voltage ladder circuit, the rung voltage levels, in terms of the voltage difference between input terminals E1 and E2, are 4.5 millivolts for the first rung, 28.3 millivolts for the second rung, 52.1 millivolts for the third rung, and 77.1 millivolts for the fourth rung. It will be apparent, however, that the particular rung levels could be chosen if desired at other levels within the range of the expected input variation. The normal voltage level between the thumbs of an average user is in the neighborhood of 20 millivolts which means that normally one light emitting diode will be lit for normal voltage levels and 2, 3 or 4 would indicate progressively higher voltage levels.

One of the principal advantages of this invention is the simplicity and low cost of the output circuit. Not only is it compact in structure and low in cost, but it is extremely easy to use. Instead of keeping track of thumb to thumb voltage in terms of millivolts, the user only has to observe the number of light emitting diodes which are lit to get a comparative voltage level. She has either a 1, 2, 3, or 4 light voltage level. This is not only easy to read, but easy to record and to compare from day to day to detect a rise in voltage. The latter factor is important because the instrument is used over a long period of time from month to month and so there will be many entries in the record and the comparison from day to day would be extremely difficult if the numbers were recorded in terms of millivolts whereas it is easy if they are recorded as either 1, 2, 3 or 4. In addition to being easy to use, the voltage ladder output circuit of this invention has the additional and more important advantage that it is low enough in cost to place the cost of the instrument within the range of the average consumer. It is estimated that the production model of this instrument will sell at retail prices in the range of $30.00 to $40.00 which is a significant reduction in the cost of the complex consumer instruments which have been proposed heretofore.

Although the voltage ladder output circuit in FIG. 1 has 4 rungs, it will be apparent to those skilled in the art that more could be added if desired. However, it is believed that 4 rungs is sufficient for the purpose of detecting the rise in voltage that accompanies ovulation.

The temperature measurement circuit portion of the instrument is shown in the bottom of FIG. 1. It includes the thermistor TP which is connected between minus 5 volts and plus 5 volts by resistors R31, R32 and R33. Thermistor TP is mounted in the end of a probe 18 (FIG. 3) which is connected to housing 10 by a small cable 20 and a plug 22. The contacts of plug 22 are shown as P1 through P4 in FIG. 1. The left side of contacts P1 and P4 are coupled to the probe. Battery 12 is located in probe 18 in this embodiment of the invention, but it will be obvious that it could be located in housing 10 if desired.

The series resistor network comprising R31, R32, and R33 is selected to have a composite value equal to the value of thermistor TP when probe 18 is in a person's mouth and potentiometer R33 is at its calibration point. The values of R31, R32 and R33 are also selected to provide a convenient adjustment range for a potentiometer R33, which has a front panel adjustment wheel 23 (see FIG. 3).

In this particular design, both ends of potentiometer R33 are coupled together to form a variable calibration adjustment which will work as well if turned to the left or to the right. It will be apparent that with both ends of potentiometer R33 coupled together and its tap coupled to R32 and R31, that the potentiometer forms two resistors in parallel. The resistance of the parallel resistors can be varied from a minimum of zero to a maximum of 500 ohms and therefore the potentiometer acts as if it were a rheostat which is variable in value from zero to 250 ohms with the exception that the variation from zero to 250 ohms is insensitive to the direction in which the calibration wheel is turned. This simplifies instructions for the user since the user can be simply told to adjust the wheel to adjust the temperature level without specifying which direction the wheel should be turned. Thermistor TP is located in the end of probe 18 and when probe 18 is inserted into a user's mouth, the user's body temperature raises the temperature of the thermistor and causes its resistance level to drop. As the resistance level of thermistor TP drops it causes the voltage on output bus 24 to drop also. The voltage on output bus 24 is measured by a voltage ladder output circuit which is functionally identical to the voltage ladder output circuit described above in connection with the voltage measurement circuit. The output indication of the voltage ladder circuit is taken from four light emitting diodes T1, T2, T3 and T4 which are a different color than the light emitting diodes V1, V2, V3 and V4. Both sets of light emitting diodes are visible on the front panel of housing 10 as shown in FIG. 3.

At least the tip of probe 18 which goes into the patient's mouth is electrically conductive and is connected electrically to the thermistor TP, which in turn is connected to the power supply, and thus forms a reference terminal ER (FIG. 1) for the voltage supply. This reference terminal forms a common mode rejection reference voltage for the differential amplifier in the voltage measurement circuit. Thus the voltage measurement circuit and the temperature measurement circuit are functionally joined together in this invention due to the fact that the probe 18 serves a function in both circuits. It serves to house the thermistor TP and to conduct the body temperature to it and it also serves as an electrical reference terminal for the common mode rejection of the differential amplifier in the voltage measurement circuit.

I claim:

1. A body voltage and temperature measuring instrument comprising:
    a housing which is sufficiently small to be held in a hand;
    two electrical terminals on said housing which are accessible from the exterior of said housing;
    a differential amplifier within said housing;
    means coupling the input of said differential amplifier to said electrical terminals;
    a first voltage ladder circuit within said housing coupled to the output of said differential amplifier;
    a first plurality of output indicators on said housing which are visible from the exterior of said housing;
    means coupling each of said output indicators to a separate rung of said voltage ladder;
    a probe;
    a temperature responsive element in said probe;
    a second voltage ladder circuit within said housing coupled to said temperature responsive element;
    a second plurality of output indicators on said housing which are visible from the exterior of said housing;
    and means coupling said second plurality of output indicators to said second voltage ladder circuit.

2. The instrument defined in claim 1 when each of said ladder circuits comprises:
    a plurality of resistors coupled together in series to form a series resistor network;
    means coupling the outermost ends of said series resistor network to different voltage levels to create a series of voltage steps at the junction of adjacent resistors;
    a plurality of voltage comparators each having two inputs and one output;
    one input of each voltage comparator being coupled to a corresponding voltage step of said series resistor network;
    the other input of each voltage comparator being coupled and parallel to the output of said differential amplifier, and
    the output of each voltage comparator being coupled to a corresponding one of said plurality of output indicators.

3. The instrument defined in claim 2 wherein said output indicators are light emitting diodes and also including a current limiting resistor coupled between each light emitting diode and the corresponding voltage comparator output.

4. The instrument defined in claim 1 and also including an inverter, means coupling the output of said differential amplifier to said inverter, and means coupling the output of said differential amplifier and inverter in parallel to said first voltage ladder circuit.

5. The instrument defined in claim 4 wherein the last mentioned means includes a pair of diodes, one coupled in series with each of said outputs.

6. The instrument defined in claim 1, wherein said temperature responsive element is a thermistor and also including a voltage source and a variable resistor coupled in series with said thermistor.

7. The instrument defined in claim 6 and also including at least two fixed resistors coupled in series between said variable resistor and said thermistor, the resistance of said variable resistor, when it is at its calibration point, plus the resistance of said fixed resistors being equal to the resistance of said thermistor when the probe is inserted into a user's mouth.

8. The instrument defined in claim 6 where said variable resistor is a potentiometer with both of its end terminals coupled together.

9. The instrument defined in claim 6 wherein said voltage source also supplies power for said differential amplifier, and also including an electrically conductive tip on the outer end of said probe and means coupling said electrically conductive tip to said voltage source to serve as a common mode rejection reference voltage for said differential amplifier.

10. The instrument defined in claim 9 wherein said power source includes a battery and wherein one terminal of said battery is coupled to said electrically conductive tip of said probe.

* * * * *